US010065464B2

(12) United States Patent
Grill et al.

(10) Patent No.: US 10,065,464 B2
(45) Date of Patent: *Sep. 4, 2018

(54) MEDICAL STIMULATION DEVICE PROVIDING NON-REGULAR ELECTRICAL STIMULATION PATTERNS FOR TREATING NEUROLOGICAL DISORDERS

(71) Applicant: Duke University, Durham, NC (US)

(72) Inventors: Warren M. Grill, Chapel Hill, NC (US); David T. Brocker, Cary, NC (US); Merril J. Birdno, Durham, NC (US)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/447,904

(22) Filed: Jul. 31, 2014

(65) Prior Publication Data
US 2014/0353944 A1 Dec. 4, 2014

Related U.S. Application Data

(63) Continuation of application No. 13/649,912, filed on Oct. 11, 2012, now Pat. No. 8,798,755, and a (Continued)

(51) Int. Cl.
*A61N 1/36* (2006.01)
*B60D 1/06* (2006.01)
*A61N 1/05* (2006.01)

(52) U.S. Cl.
CPC ......... *B60D 1/065* (2013.01); *A61N 1/36067* (2013.01); *A61N 1/36082* (2013.01);
(Continued)

(58) Field of Classification Search
CPC .......... A61N 1/361961; A61N 1/36175; A61N 1/36178; A61N 1/36082; A61N 1/36189; A61N 1/36014; A61N 1/36067
(Continued)

(56) References Cited

U.S. PATENT DOCUMENTS 3,833,005 A 9/1974 Wingrove
4,338,945 A 7/1982 Kosugi et al.
(Continued)

FOREIGN PATENT DOCUMENTS

EP 1145735 10/2001
WO WO2010/039274 4/2010

OTHER PUBLICATIONS

Benabid, A., et al, "Long-Term Suppression of Tremor by Chronic Stimulation of the Ventral Intermediate Thalamic Nucleus," Lancet. 337:403-6 (Feb. 16, 1991).
(Continued)

*Primary Examiner* — Paula J Stice
(74) *Attorney, Agent, or Firm* — McDonald Hopkins LLC

(57) ABSTRACT

Systems and methods for stimulation of neurological tissue and generation stimulation trains with temporal patterns of stimulation, in which the interval between electrical pulses (the inter-pulse intervals) changes or varies over time. The features of the stimulation trains may be selected and arranged algorithmically to by clinical trial. These stimulation trains are generated to target a specific neurological disorder, by arranging sets of features which reduce symptoms of that neurological disorder into a pattern which is effective at reducing those symptoms while maintaining or reducing power consumption versus regular stimulation signals. Compared to conventional continuous, high rate pulse trains having regular (i.e., constant) inter-pulse intervals, the non-regular (i.e., not constant) pulse patterns or trains that embody features of the invention provide increased efficacy and/or a lower than average frequency.

7 Claims, 14 Drawing Sheets

Related U.S. Application Data continuation-in-part of application No. 12/587,295, filed on Oct. 5, 2009, now Pat. No. 8,447,405.

(60) Provisional application No. 61/558,871, filed on Nov. 11, 2011, provisional application No. 61/545,971, filed on Oct. 11, 2011, provisional application No. 61/102,575, filed on Oct. 3, 2008.

(52) U.S. Cl.
CPC ..... *A61N 1/36178* (2013.01); *A61N 1/36189* (2013.01); *A61N 1/0534* (2013.01); *A61N 1/36196* (2013.01)

(58) Field of Classification Search
USPC .................................. 607/66, 68, 70, 72, 73
See application file for complete search history.

(56) References Cited

U.S. PATENT DOCUMENTS

| | | | |
|---|---|---|---|
| 5,018,524 | A | 5/1991 | Gu et al. |
| 5,095,904 | A | 3/1992 | Seligman et al. |
| 5,716,377 | A | 2/1998 | Rise et al. |
| 6,560,490 | B2 | 5/2003 | Grill et al. |
| 6,944,501 | B1 * | 9/2005 | Pless ............................. 607/45 |
| 7,010,351 | B2 | 3/2006 | Firlik et al. |
| 7,191,014 | B2 | 3/2007 | Kobayashi et al. |
| 8,073,544 | B2 | 12/2011 | Pless |
| 8,355,789 | B2 * | 1/2013 | Werder .............. A61N 1/36017 607/45 |
| 8,447,405 | B2 * | 5/2013 | Grill et al. ...................... 607/45 |
| 8,798,755 | B2 * | 8/2014 | Grill et al. ...................... 607/45 |
| 2002/0177882 | A1 | 11/2002 | DiLorenzo |
| 2003/0135248 | A1 | 7/2003 | Stypulkowski |
| 2003/0139248 | A1 | 7/2003 | Rogers et al. |
| 2004/0158298 | A1 | 8/2004 | Gliner |
| 2004/0249422 | A1 | 12/2004 | Gliner et al. |
| 2005/0060009 | A1 | 3/2005 | Goetz |
| 2005/0222641 | A1 | 10/2005 | Pless |
| 2005/0228461 | A1 | 10/2005 | Osorio et al. |
| 2006/0015153 | A1 * | 1/2006 | Gliner .................. A61N 1/3606 607/45 |
| 2007/0288064 | A1 | 12/2007 | Butson |
| 2009/0131993 | A1 | 5/2009 | Rousso et al. |
| 2010/0121416 | A1 | 5/2010 | Lee |
| 2010/0152807 | A1 | 6/2010 | Grill et al. |
| 2011/0093041 | A1 | 4/2011 | Straka et al. |

OTHER PUBLICATIONS

Birdno, M.J., "Analyzing the mechanisms of thalamic deep brain stimulation: computational and clinical studies," Ph. D. Dissertation, Department of Biomedical Engineering, Duke University, Durham, NC, USA (Aug. 2009).

Constantoyannis, C., et al, "Tremor induced by thalamic deep brain stimulation in patients with complex regional facial pain," Movement Disorders vol. 19, No. 8, 19:933-936. (2004).

Davis, L, "Handbook of Genetic Algorithms" Van Nostrand Reinhold, NY (1991).

Dorval, A. D., et al., "Deep Brain Stimulation Alleviates Parkinsonian Bradykinesia by Regularizing Thalamic Throughput in Human Subjects,". Society for Neuroscience Abstracts 32. (2007), J Neurophysiol 104: 911-921 (Aug. 2010, First published May 26, 2010).

Feng, X., et al, "Optimal Deep Brain Stimulation of the Subthalamic Nucleus-A Computational Study," J Comput Neurosci. 23(3):265-282 (Jan. 9, 2007).

Fogelson, N. et al, "Frequency Dependent Effects of Subthalamic Nucleus Stimulation in Parkinson's Disease," Neuroscience Letters 382:5-9 (2005).

Grefenstette, J. J., "Optimization of Control Parameters for Genetic Algorithms," IEEE Transactions on Systems, Man and Cybernetics 16:122-128 (1986).

Grill, W.M. et al, "Effect of Stimulus Waveform on Tremor Suppression and Paresthesias Evoked by Thalamic Deep Brain Stimulation," Society for Neuroscience Abstracts 29 (2003).

International Search Report and the Written Opinion of the International Searching Authority in corresponding PCT application No. PCT/US09/05459 dated (Dec. 3, 2009).

Kuncel, A. M. et al., "Clinical Response to Varying the Stimulus Parameters in Deep Brain Stimulation for Essential Tremor," Movement Disorders 21(11):1920-1928 (2006).

Kupsch, A. et al., "The effects of frequency in pallidal deep brain stimulation for primary dystonia," J Neurol 250:1201-1204 (2003).

Limousin, P. et al, "Effect on Parkinsonian signs and symptoms of bilateral stimulation," The Lancet 345:91-95 (1995).

McIntyre, C.C., et al., "Cellular effects of deep brain stimulation: model-based analysis of activation and inhibition," J Neurophysiol 91:1457-1469 (2004).

Rubin ,J.E. et al, "High Frequency Stimulation of the Subthalamic Nucleus Eliminates Pathological Thalamic Rhythmicity in a Computational Model,". J.Comput. Neurosci. 16:211-235 (2004).

Timmermann, L. et al, "The cerebral oscillatory network of parkinsonian resting tremor," Brain, 126:199-212 (2003).

Extended European Search Report for Application 13875748.9 PCT/US2013046183, dated Mar. 9, 2016, European Patent Office, Germany.

International Search Report and the Written Opinion of the International Searching Authority, PCT/US2013/046183, Duke University, dated Oct. 4, 2013.

International Search Report and the Written Opinion of the International Searching Authority, PCT/US2012/059787, Duke University, dated Jan. 4, 2013.

* cited by examiner

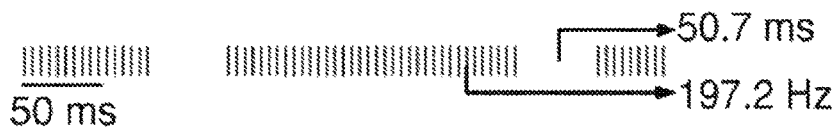
$\overline{50\ ms}$
→ 50.7 ms
→ 197.2 Hz
Fig. 7C
→ 285.3 Hz
→ 142.7 Hz
Fig. 7D
| Pattern | Geometric Mean (Hz) | Entropy (bits/pulse) | MPR (Hz) | Mean(IPF) (Hz) | CV(IPF) | CV(IPI) |
|---|---|---|---|---|---|---|
| Absence | 185 | 0.18 | 158 | 192 | 0.15 | 1.19 |
| Presence | 185 | 0.95 | 176 | 196 | 0.35 | 0.30 |
| Regular | 185 | 0 | 185 | 185 | 0 | 0 |
| Uniform | 185 | 5.6 | 169 | 201 | 0.42 | 0.41 |
| Unipeak | 185 | 5.5 | 145 | 234 | 0.72 | 0.73 |
Fig. 8

| Patient | Sex | Age | Hemisphere | Target | Off Meds (12 hr) |
|---------|-----|-----|------------|--------|------------------|
| 1 | F | 54 | Right | STN | Yes |
| 2 | M | 59 | Right | GPi | Yes |
| 3 | M | 59 | Left | STN | Yes |
| 4 | M | 65 | Left | STN | No |
| 5 | F | 61 | Left | STN | No |
| 6 | F | 64 | Left | GPi | No |
| 7 | F | 59 | Right | GPi | Yes |
| 8 | M | 66 | Left | STN | No |
| 9 | M | 52 | Left | STN | No |
| 10 | M | 57 | Right | STN | Yes |
*Fig. 9*
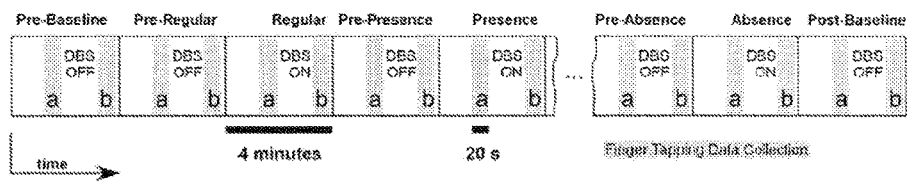
*Fig. 10A*
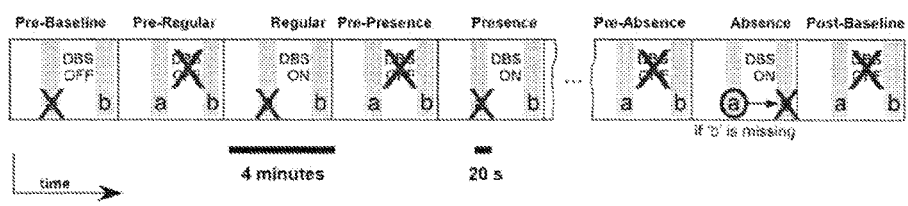
*Fig. 10B*

MEDICAL STIMULATION DEVICE PROVIDING NON-REGULAR ELECTRICAL STIMULATION PATTERNS FOR TREATING NEUROLOGICAL DISORDERS

CROSS-REFERENCE TO RELATED APPLICATION

This application is a continuation of U.S. patent application Ser. No. 13/649,912 now U.S. Pat. No. 8,798,755, entitled "Non-Regular Electrical Stimulation Patterns For Treating Neurological Disorders", filed Oct. 11, 2012, which claims the benefit of U.S. Provisional Patent Application Ser. No. 61/558,871, filed Nov. 11, 2011, and entitled "Non-Regular Electrical Stimulation Patterns for Treating Neurological Disorders," and also claims the benefit of U.S. Provisional Patent Application Ser. No. 61/545,791, filed Oct. 11, 2011, and entitled "Non-Regular Patterns of Deep Brain Stimulation for the Suppression of Neurological Disorder Symptoms," and was also a continuation-in-part of pending U.S. patent application Ser. No. 12/587,295, now U.S. Pat. No. 8,447,405, filed Oct. 5, 2009, and entitled "Non-Regular Electrical Stimulation Patterns for Treating Neurological Disorders," which claims the benefit of U.S. Provisional Patent Application Ser. No. 61/102,575, filed Oct. 3, 2008; and entitled "Stimulation Patterns For Treating Neurological Disorders Via Deep Brain Stimulation," all of which are incorporated herein in their entirety by reference.

BACKGROUND OF THE INVENTION

Systems and methods according to the present invention relate generally to neural stimulation in animals, including humans. Deep Brain Stimulation (DBS) has been found to be successful in treating a variety of neurological disorders, including movement disorders. High frequency DBS in the internal segment of the globus pallidus (GPi) or subthalamic nucleus (STN) is an effective and adjustable surgical treatment for motor symptoms of advanced Parkinson's disease (PD). DBS reduces tremor, rigidity, akinesia, and postural instability, and allows levodopa doses to be decreased. Patients clinically diagnosed with idiopathic PD suffering from the cardinal motor symptoms are likely to receive benefit from DBS, with levodopa responsiveness predictive of its efficacy. Similarly, high frequency DBS in the ventral intermediate nucleus (Vim) of the thalamus is an effective and adjustable surgical treatment for tremor in persons with essential tremor or multiple sclerosis. As well, DBS is used to treat a broad range of neurological and psychiatric disorders including but not limited to epilepsy, dystonia, obsessive compulsive disorder, depression, Tourette's syndrome, addiction, and Alzheimer's disease.

Generally, such treatment involves placement of a DBS type lead into a targeted region of the brain through a burr hole drilled in the patient's skull, and the application of appropriate stimulation through the lead to the targeted region.

Presently, in DBS, beneficial (symptom-relieving) effects are observed primarily at high stimulation frequencies above 100 Hz that are delivered in stimulation patterns or trains in which the interval between electrical pulses (the inter-pulse intervals) is constant over time. The trace of a conventional stimulation train for DBS is shown in FIG. 2. The beneficial effects of DBS on symptoms are only observed at high frequencies, while low frequency stimulation may exacerbate symptoms. Thalamic DBS at less than or equal to 50 Hz has been shown to increase tremor in patients with essential tremor (ET). Similarly, 50 Hz DBS has been shown to produce tremor in pain patients receiving simulation of the ventral posterior medial nucleus of the thalamus (VPM), but the tremor disappears when the frequency is increased. Likewise, DBS of the subthalamic nucleus (STN) at 10 Hz has been shown to worsen akinesia in patients with while DBS at 130 Hz has been shown to improve motor function. Similarly, stimulation of the globus pallidus (GPi) at or above 130 Hz has been shown to improve dystonia, whereas stimulation at either 5 or 50 Hz leads to significant worsening.

In patients with ET, random patterns of stimulation are less effective at relieving tremor than regular patterns of stimulation. Similarly, in patients with PD, random patterns of stimulation are less effective at relieving bradykinesia than regular patterns of stimulation. In patients with ET, non-regular stimulation patterns are less effective at suppressing tremor than temporally regular stimulation because sufficiently long gaps in the stimulation train allow pathological activity to propagate through the stimulated nucleus. However, the features of non-regular stimulation patterns that influence clinical efficacy in PD are unknown.

Model studies also indicate that the masking of pathological burst activity occurs only with sufficiently high stimulation frequencies. Responsiveness of tremor to changes in DBS amplitude and frequency are strongly correlated with the ability of applied stimuli to mask neuronal bursting.

Although effective, conventional high frequency stimulation generates stronger side-effects than low frequency stimulation, and the therapeutic window between the voltage that generates the desired clinical effect(s) and the voltage that generates undesired side effects decreases with increasing frequency. Precise lead placement therefore becomes important. Further, high stimulation frequencies increase power consumption. The need for higher frequencies and increased power consumption shortens the useful lifetime and/or increases the physical size of battery-powered implantable pulse generators. The need for higher frequencies and increased power consumption requires a larger battery size, and frequent charging of the battery, if the battery is rechargeable. Thus, the art of DBS would benefit from systems and methods having significantly increased efficacy over prior Regular stimulation while reducing, or minimizing impact on, battery life.

SUMMARY OF THE INVENTION

One aspect of the present invention is to provide a temporal pattern of stimulation for application to targeted neurological tissue comprising a repeating succession of non-regular pulse trains, each pulse train comprising a plurality of evenly spaced pulses and at least one pulse feature.

Another aspect of the present invention is to provide a method of generating series of stimulation signals for the treatment of a neurological disorder comprising: selecting a neurological disorder with one or more symptoms to be treated by the stimulation signals; identifying pulse features of the stimulation signals that suppress one or more symptoms of the neurological disorder when applied to specific areas of a neurological tissue; selecting one or more patterns of non-regular stimulation signals comprised of the pulse features; and generating a pulse train of stimulation signals including the one or more selected patterns.

An additional aspect of the invention is to provide a method for stimulation of a targeted neurological tissue region comprising applying a non-regular pulse train, each pulse train comprising a plurality of evenly spaced pulses and at least one pulse feature and repeating the pulse train in succession.

BRIEF DESCRIPTION OF THE DRAWINGS

FIG. 7C depicts an "Absence" stimulation pattern train according to the present invention.

FIG. 7D depicts a "Presence" stimulation pattern train according to the present invention.

FIG. 8 is a table of stimulation pattern train parameters.

FIG. 9 is a table of patient data.

FIG. 10A is a timeline depicting stimulation response data collection.

FIG. 10B is a timeline depicting stimulation response data analysis.

DESCRIPTION OF THE PREFERRED EMBODIMENTS

Although the disclosure hereof is detailed and exact to enable those skilled in the art to practice the invention, the physical embodiments herein disclosed merely exemplify the invention, which may be embodied in other specific structures. While the preferred embodiment has been described, the details may be changed without departing from the invention, which is defined by the claims.

Figure 1:
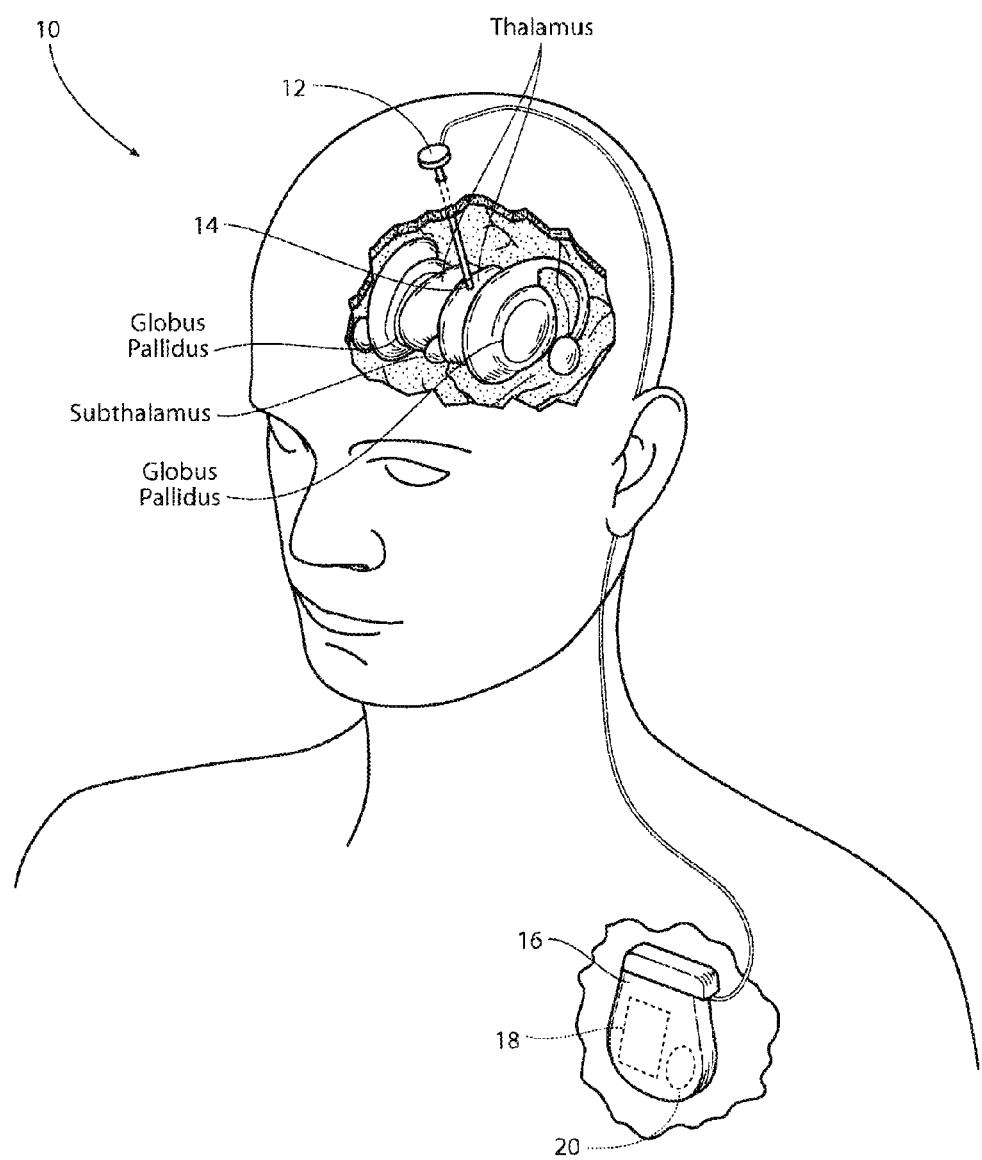
FIG. 1 is an anatomic view of a system for stimulating tissue of the central nervous system that includes an lead implanted in brain tissue coupled to a pulse generator that is programmed to provide non-regular (i.e., not constant) pulse patterns or trains, in which the interval between electrical pulses (the inter-pulse intervals) changes or varies over time.

FIG. 1 is a system 10 for stimulating tissue of the central nervous system. The system includes a lead 12 placed in a desired position in contact with central nervous system tissue. In the illustrated embodiment, the lead 12 is implanted in a region of the brain, such as the thalamus, subthalamus, or globus pallidus for the purpose of deep brain stimulation. However, it should be understood, the lead 12 could be implanted in, on, or near the spinal cord; or in, on, or near a peripheral nerve (sensory or motor) for the purpose of selective stimulation to achieve a therapeutic purpose.

The distal end of the lead 12 carries one or more electrodes 14 to apply electrical pulses to the targeted tissue region. The electrical pulses are supplied by a pulse generator 16 coupled to the lead 12.

In the illustrated embodiment, the pulse generator 16 is implanted in a suitable location remote from the lead 12, e.g., in the shoulder region. It should be appreciated, however, that the pulse generator 16 could be placed in other regions of the body or externally.

When implanted, the case of the pulse generator can serve as a reference or return electrode. Alternatively, the lead 12 can include a reference or return electrode (comprising a bi-polar arrangement), or a separate reference or return electrode can be implanted or attached elsewhere on the body (comprising a mono-polar arrangement).

The pulse generator 16 includes an on-board, programmable microprocessor 18, which carries embedded code. The code expresses pre-programmed rules or algorithms under which a desired electrical stimulation waveform pattern or train is generated and distributed to the electrode(s) 14 on the lead 12. According to these programmed rules, the pulse generator 16 directs the prescribed stimulation waveform patterns or trains through the lead 12 to the electrode(s) 14, which serve to stimulate selectively the targeted tissue region. The code is preprogrammed by a clinician to achieve the particular physiologic response desired.

In the illustrated embodiment, an on-board battery 20 supplies power to the microprocessor 18. Currently, batteries 20 must be replaced every 1 to 9 years, depending on the stimulation parameters needed to treat a disorder. When the battery life ends, the replacement of batteries requires another invasive surgical procedure to gain access to the implanted pulse generator. As will be described, the system 10 makes possible, among its several benefits, an increase in battery life.

Figure 2:
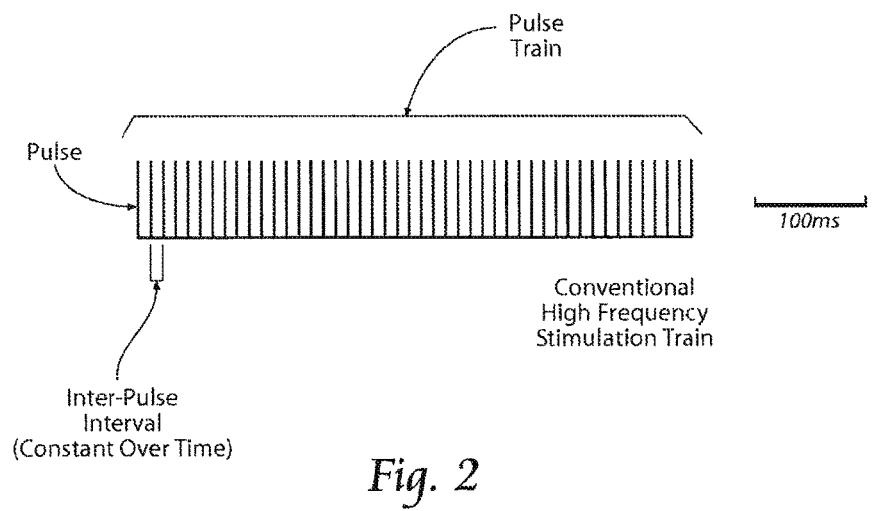
FIG. 2 is a diagrammatic trace that shows a conventional regular high frequency stimulation train, in which the interval between electrical pulses (the inter-pulse intervals) is constant.
Figure 3:
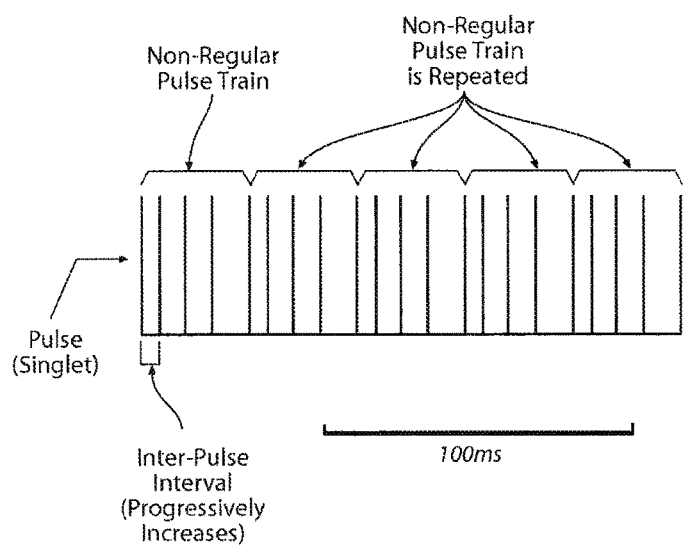
FIG. 3 is a diagrammatic trace showing a representative example of a repeating non-regular pulse pattern or train in which the inter-pulse intervals are linearly cyclically ramped over time.
Figure 4:
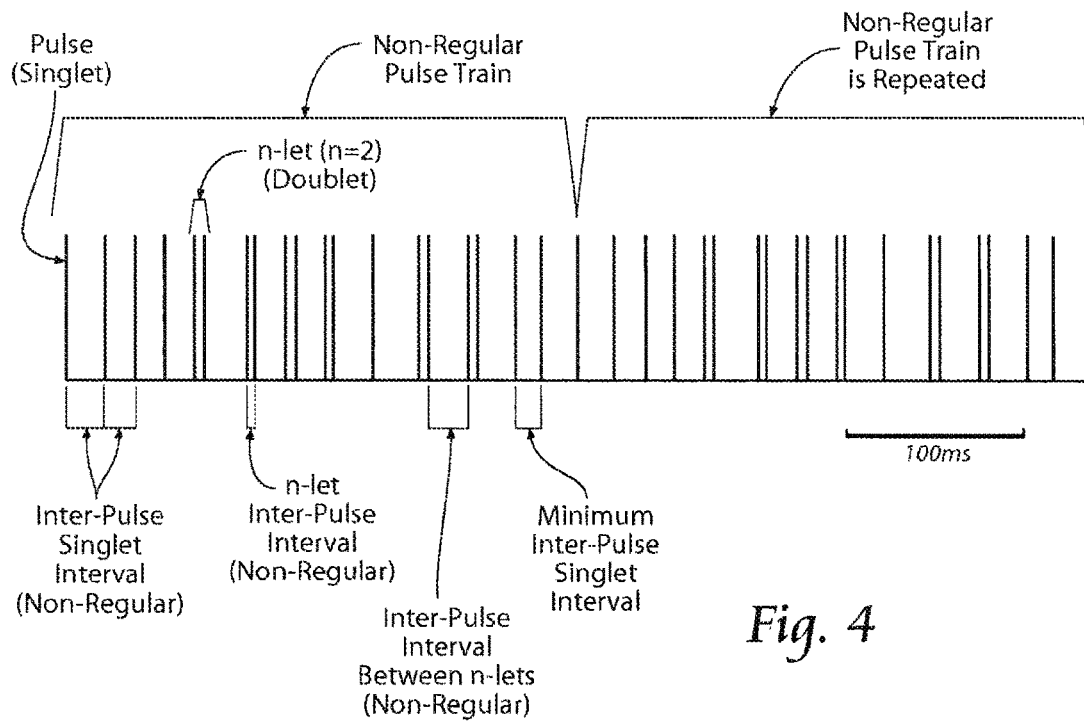
FIGS. 4 and 5 are diagrammatic traces showing other representative examples of repeating non-regular pulse patterns or trains comprising within, a single pulse train, a combination of single pulses (singlets) and embedded multiple pulse groups (n-lets), with non-regular inter-pulse intervals between singlets and n-lets as well as non-regular inter-pulse intervals within the multiple pulse n-lets.
Figure 5:
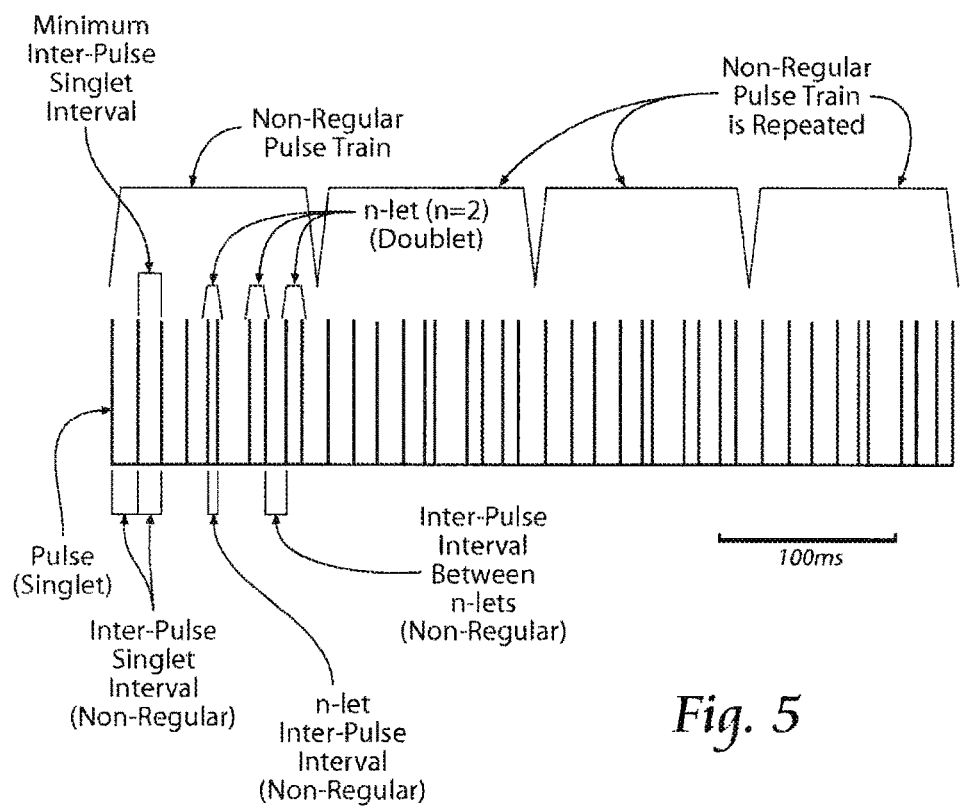

The stimulation waveform pattern or train generated by the pulse generator differs from convention pulse patterns or trains in that the temporal pattern of stimulation comprises repeating non-regular (i.e., not constant) pulse patterns or trains, in which the interval between electrical pulses (the inter-pulse intervals or IPI) changes or varies over time. Examples of these repeating non-regular pulse patterns or trains are shown in FIGS. 3 to 5. Compared to conventional pulse trains having regular (i.e., constant) inter-pulse intervals (as shown in FIG. 2), the non-regular (i.e., not constant) pulse patterns or trains provide a lower average frequency for a given pulse pattern or train, where the average frequency for a given pulse train (expressed in hertz or Hz) is defined as the sum of the inter-pulse intervals for the pulse train in seconds ($\Sigma_{IPI}$) divided by the number of pulses (n) in the given pulse train, or ($\Sigma_{IPI}$)/n. A lower average frequency makes possible a reduction in the intensity of side effects, as well as an increase in the dynamic range between the onset of the desired clinical effect(s) and side effects, thereby increasing the clinical efficacy and reducing sensitivity to the position of the electrode(s). A lower average frequency brought about by a non-regular pulse pattern or train also leads to a decrease in power consumption, thereby prolonging battery life and reducing battery size.

The repeating non-regular (i.e., not constant) pulse patterns or trains can take a variety of different firms. For example, as will be described in greater detail later, the inter-pulse intervals can be linearly cyclically ramped over time in non-regular temporal patterns (growing larger and/or smaller or a combination of each over time); or be periodically embedded in non-regular temporal patterns comprising clusters or groups of multiple pulses (called n-lets), wherein n is two or more. For example, when n=2, the n-let can be called a doublet; when n=3, the n-let can be called a triplet; when n=4, the n-let can be called a quadlet; and so on. The repeating non-regular pulse patterns or rains can comprise combinations of single pulses (called singlets) spaced apart by varying non-regular inter-pulse intervals and n-lets interspersed among the singlets, the n-lets themselves being spaced apart by varying non-regular inter-pulse intervals both between adjacent n-lets and between the n pulses embedded in the n-let. If desired, the non-regularity of the pulse pattern or train can be accompanied by concomitant changes in waveform and/or amplitude, and/or duration in each pulse pattern or train or in successive pulse patterns or trains.

Each pulse comprising a singlet or imbedded in an n-let in a given train comprises a waveform that can be monophasic, biphasic, or multiphasic. Each waveform possesses a given amplitude (expressed, e.g., in amperes or volts) that can, by way of example, range from 10 μa ($E^{-6}$) to 10 ma ($E^{-3}$). The amplitude of a given phase in a waveform can be the same or differ among the phases. Each waveform also possesses a duration (expressed, e.g., seconds) that can, by way of example, range from 10 μs ($E^{-6}$) to 2 ms ($E^{-3}$). The duration of the phases in a given waveform can likewise be the same or different. It is emphasized that all numerical values expressed herein are given by way of example only. They can be varied, increased or decreased, according to the clinical objectives.

When applied in deep brain stimulation, it is believed that repeating stimulation patterns or trains applied with non-regular inter-pulse intervals can regularize the output of disordered neuronal firing, to thereby prevent the generation and propagation of bursting activity with a lower average stimulation frequency than required with conventional constant frequency trains, i.e., with a lower average frequency than about 100 Hz.

FIG. 3 shows a representative example of a repeating non-regular pulse pattern or train in which the inter-pulse intervals are linearly cyclically ramped over time. As shown in FIG. 3, the pulse pattern or train includes singlet pulses (singlets) spaced apart by progressively increasing inter-pulse intervals providing a decrease in frequency over time, e.g., having an initial instantaneous frequency of 140 Hz, decreasing with doubling inter-pulse intervals, to a final instantaneous frequency of 40 Hz. The inter-pulse intervals can vary within a specified range selected based upon clinical objectives, e.g., not to exceed 25 ms, or not to exceed 100 ms, or not to exceed 200 ms, to take into account burst responses and subsequent disruption of thalamic fidelity). The non-regular pulse trains repeat themselves fir a clinically appropriate period of time. As shown in FIG. 3, the first pulse train comprises progressively increasing inter-pulse intervals from smallest to largest, followed immediately by another essentially identical second pulse train comprising progressively increasing inter-pulse intervals from smallest to largest, followed immediately by an essentially identical third pulse train, and so on. Therefore, between successive pulse trains, there is an instantaneous change from the largest inter-pulse interval (at the end of one train) to the smallest inter-pulse interval (at the beginning of the next successive train). The train shown in FIG. 3 has an average frequency of 85 Hz and is highly non-regular, with a coefficient of variation (CV) of about 0.5. As is demonstrated in the following Example (Batch 3), the increased efficiency of the pulse train shown in FIG. 3 (due to the lower average frequency) also can provide greater efficacy, as compared to a constant 100 Hz pulse pattern.

The train shown in FIG. 3 exploits the dynamics of burst generation in thalamic neurons. The early high frequency phase of the train masks intrinsic activity in subthalamic nucleus (STN) neurons, and the inter-pulse interval increases reduce the average frequency. A family of trains can be provided by varying the initial frequency, final frequency, and rate of change within the train, with the objective to prevent thalamic bursting with a lower average stimulation frequency than required with constant frequency trains.

FIGS. 4 and 5 show other representative examples of repeating non-regular pulse patterns or trains. The pulse trains in FIGS. 4 and 5 comprise within, a single pulse train, a combination of single pulses (singlets) and embedded multiple pulse groups (n-lets), with non-regular inter-pulse intervals between singlets and n-lets, as well as non-regular inter-pulse intervals within the n-lets themselves. The non-regular pulse trains repeat themselves for a clinically appropriate period of time.

The non-regular pulse train can be characterized as comprising one or more singlets spaced apart by a minimum inter-pulse singlet interval and one or more n-lets comprising, for each n-let, two or more pulses spaced apart by an inter-pulse interval (called the "n-let inter-pulse interval") that is less than the minimum singlet inter-pulse interval. The n-let inter-pulse interval can itself vary within the train, as can the interval between successive n-lets or a successive n-lets and singlets. The non-regular pulse trains comprising singlets and n-lets repeat themselves for a clinically appropriate period of time.

In FIG. 4, each pulse train comprises four singlets in succession (with non-regular inter-pulse intervals there between); followed by four doublets in succession (with non-regular inter-doublet pulse intervals there between and non-regular inter-pulse intervals within each n-let); followed by a singlet, three doublets, and a singlet (with non-regular inter-pulse intervals there between and non-regular inter-pulse intervals within each n-let). The temporal pattern of this pulse train repeats itself in succession for a clinically appropriate period of time. The non-regular temporal pulse pattern shown in FIG. 4 has an average frequency of 67.82 Hz without loss of efficacy.

In FIG. 5, each pulse train comprises four singlets in succession (with non-regular inter-pulse intervals there between); followed by three doublets in succession (with non-regular inter-doublet pulse intervals there between and non-regular inter-pulse intervals within each n-let). The temporal pattern of this pulse train repeats itself in succession for a clinically appropriate period of time. The non-regular temporal pulse pattern shown in FIG. 5 has an average frequency of 87.62 Hz without loss of efficacy.

Computational models of thalamic DBS and subthalamic DBS can be used with genetic-algorithm-based optimization (GA) to design non-regular stimulation patterns or trains that produce desired relief of symptoms with a lower average stimulation frequency than regular, high-rate stimulation. McIntyre et al. 2004 (Appendix A, hereto), Birdno, 2009 (Appendix B, hereto); Rubin and Terman, 2004 (Appendix C, hereto); and Davis L (1991) Handbook of genetic algorithms, Van Nostrand Reinhold, NY, are incorporated herein by reference.

Possible mechanisms at the cellular and systems level may explain the effectiveness using non-regular patterns of stimulation for the treatment of patients with neurological disorders. At a cellular level the use of non-regular stimulation of the nervous system may rely on the possibility that neurons are sensitive to the specific timing of the stimulation pulses. In other words, if the specific timing of the stimulation is important to individual neurons or even a population of neurons, it may be advantageous for DBS systems to use non-regular temporal patterns of stimulation to exploit this sensitivity and/or reactivity. In the branch of neuroscience concerned with the neural code (i.e. how neurons communicate information with one another) the importance of the timing of inputs to a neuron as it relates to information transfer in the system is a common idea that is termed temporal (or spatiotemporal) coding. At a systems level, a non-regular stimulation pattern could be more effective than regular stimulation at disrupting or reversing pathological features of a neurological disorder such as Parkinson's disease. For example, a non-regular pattern of stimulation may be able effectively to break up pathological synchronization and oscillations that are common in systems affected by PD. Exploiting the neural coding by taking advantage of the brain's sensitivity, at any level, to the temporal structure of stimulation makes the technology described herein different than any other stimulation protocol ever developed to treat neurological disorders.

The technology described herein differs from prior systems and methods by utilizing non-regular stimulation with a higher average frequency (greater than about 100 Hz, and preferably less than about 250 Hz) to gain a clinical benefit greater than what can be elicited with regular high frequency stimulation.

Figure 6:
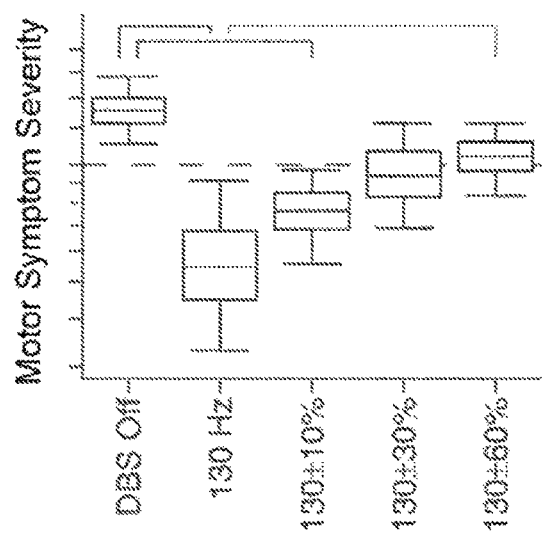
FIG. 6 depicts prior experimentation showing decreased efficacy in reducing symptoms as the variability of random patterns of DBS increases, hick is modified from Dorval et al. (2010).
Figure 15:
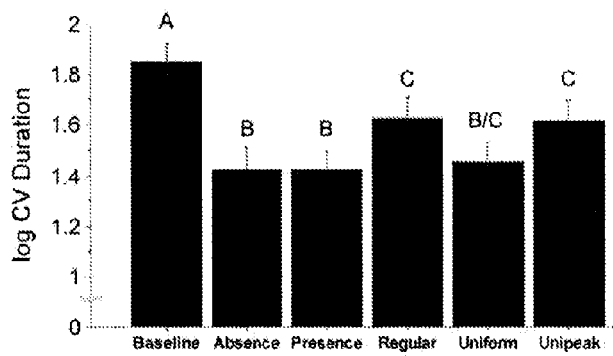
FIG. 15 is a bar graph showing statistically significant changes motor symptom severity as assessed through the coefficient of variation of click duration across different temporal patterns of stimulation according to the present invention.

While non-regular patterns of DBS have been tested in patients with PD in the past, the objective was to elucidate the mechanisms of DBS and the importance of the pattern of stimulation for the efficacy of the therapy. Results showed that the more non-regular you made randomly generated patterns of stimulation, the more ineffective that stimulation became at suppressing motor symptoms in Parkinson's disease patients (FIG. 6). It was not until more structured patterns of stimulation designed to expose the effects of certain characteristics of the stimulation were tested that non-regular, higher frequency patterns of stimulation that were found to improve significantly a measure of motor performance when compared to regular stimulation at a comparable frequency (FIG. 15).

Others have proposed using non-regular patterns of stimulation (generated from non-linear dynamics) in mammals, and such methods seem to be effective in a mouse model of a minimally conscious state. While such results may be interesting, they are not in human patients, and the stimulation patterns were generated through different means. Indeed, results in human patients with ET and in human patients with PD show that such random patterns of stimulation are not effective in relieving symptoms. Patterns of stimulation according to the present invention are generated in a different way and are preferably structured and repeating. It has been found that features of non-regular patterns of DBS may need to be carefully chosen for the treatment of a specific neurological disorder in order to have the desired effects. For instance, a stimulation pattern that works for the treatment of PD may not be efficacious in treating essential tremor (ET) and/or vice versa.

Stimulation pulses and methods according to the present invention may be implemented in an implantable pulse generator capable of producing desirable patterns of the non-regular stimulation. Known DBS devices, or similar variations thereof, may be used and programmed to generate the novel stimulation patterns described here herein.

Working Example

This invention has been used in treating or relieving symptoms of Parkinson's disease. The patterns of stimulation were designed to expose the effects of certain characteristics of the stimulation and yielded non-regular, high-frequency patterns of stimulation that significantly improved motor performance when compared to regular stimulation at a comparable frequency.

The way in which the non-regular patterns of stimulation were designed and/or configured for the present working example differentiates the present methodology from all previous work regarding electrical stimulation for the treatment of PD. The non-regular patterns of stimulation were chosen because they contained features that may be important to the neural code in the DBS target area. These features included: bursts, pauses, gradual increments and/or decrements in the interpulse interval, and other pulse structures thought to be important for communicating information between neurons in the brain.

Figure 7A:
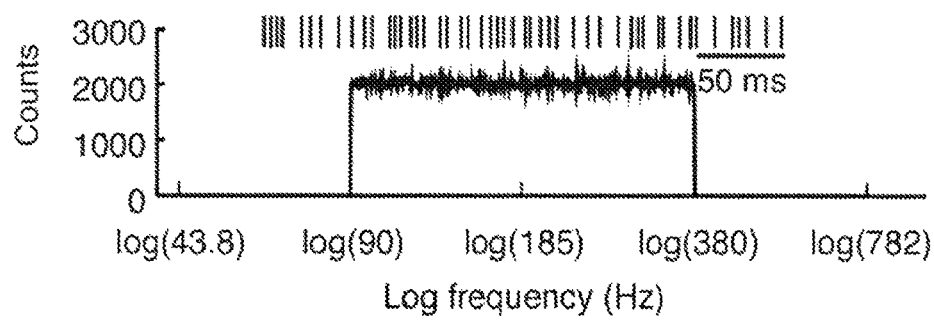
FIG. 7A depicts a "Uniform" stimulation pattern train according to the present invention.

In the PD example, after failing to find randomly generated non-regular patterns of stimulation capable of increasing the efficacy of DBS compared to conventional regular pattern of stimulation, non-regular patterns of stimulation were designed to elucidate the effects of certain characteristics of the stimulation pattern. For example, a stimulation pattern was created, wherein such pattern included bursts of stimulation pulses in rapid succession separated by groups of evenly spaced stimulation pulses (see FIG. 7D). These novel patterns of stimulation where tested using intraoperative experiments. These intraoperative experiments were conducted by connecting to an exposed lead of DBS electrodes implanted in a human, then delivering the patterns of stimulation. Motor impairment was then quantified while delivering the patterns of stimulation using a finger-tapping task.

The results that certain of these trains or temporal patterns of stimulation provided greater treatment of symptoms that regular high frequency stimulation were unexpected. FIG. 6 shows prior experimentation, which indicated that greater variability in DBS stimulation pulse trains resulted in increased motor symptom severity. The stimulation applied included randomly generated, gamma distributed inter-pulse intervals. Following such results, what was expected in the present implementation was that non-regular stimulation would worsen motor symptoms.

FIGS. 7A-7D depict various non-regular stimulation patterns applied to humans according to the present invention. The first stimulation pattern, in FIG. 7A, may be referred to as a Uniform temporally non-regular stimulation. The Uniform stimulation pulse train includes non-regular timing between stimulation pulses, but does not include stimulation bursts or pauses. As used herein, a stimulation pulse burst is defined as an occurrence of at least two consecutive instantaneous pulse frequencies (IPF's) ($IPF_i$ and $IPF_{i+1}$) greater than $2*IPF_m$, where $IPF_m$ is the average IPF over some period of time preceding $IPF_i$, such as about 125 milliseconds. As used herein, a stimulation pulse pause is defined as an IPF that is lower than a desired frequency, such as lower than the minimum frequency at which DBS effectively suppresses tremor, which may be about 90 Hz. Another way of explaining a pulse pause is a desirable period of time, such as about 11 milliseconds, that passes without the initiation of a stimulation pulse. The Uniform pulse train may be said to be characterized by a log-uniform distribution of instantaneous pulse frequencies (IPFs).

Figure 7B:
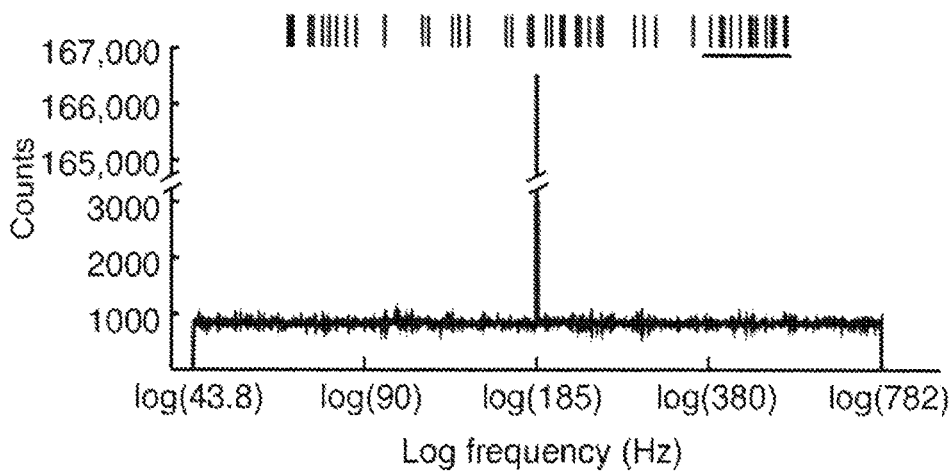
FIG. 7B depicts a "Unipeak" stimulation train according to the present invention.

FIG. 7B depicts what may be referred to as a Unipeak stimulation pulse train, which includes a wider log-uniform distribution of instantaneous pulse frequencies, including some pulse train bursts and some pulse train pauses.

FIG. 7C depicts a stimulation pulse train, which may be termed the Absence train, which included a regular, periodic stimulation, but including pulse train pauses, but no pulse train bursts.

FIG. 7D shows another stimulation pulse train, which may be referred to as the Presence train, which included a regular, periodic stimulation, and further including pulse train bursts, but no pulse train pauses.

FIG. 8 provides a summary table of the properties of the above-discussed stimulation trains, as well as a Regular stimulation train of periodic stimulation provided at 185 Hz. In the table, MPR refers to mean pulse rate, expressed in Hertz. Mean(IPF) is the mean instantaneous pulse frequency, calculated by the following equation:

$$\Sigma i = 1 n - 1 \square (1/IPIi) n - 1$$

where n equals the number of stimulation pulses in the pulse train, and IPI equals the inter-pulse interval, or time between the start of pulse number i and pulse number i+1 in the pulse train. Also in the table in FIG. 8, the coefficient of variation of the stimulation pulse trains' IPF and IPI is provided, where the coefficient of variation is defined by the standard deviation of the respective variable (IPF or IPI) divided by the mean of the respective variable.

Ten patients completed the experimental study and were included in the data analysis. The table shown in FIG. 9 discloses some patient data. In the Target column of the table, STN refers to a target site of stimulation including the patient's subthalamic nucleus and GPi refers to a target site of stimulation including the patient's globus pallidus interna.

In the experimental study the Absence and Presence patterns were both periodic with low entropy (<1 bits/pulse) and characterized by either short periods absent of pulses or the presence of short bursts of pulses, respectively. The pauses and bursts both occurred at 4.4 Hz. The Uniform and Unipeak patterns were highly irregular (high entropy: ~5.5-5.6 bits/pulse) and were created from log-uniform distributions of IPFs. Although the Unipeak pattern was created from a wider log-uniform distribution of IPFs (44-720 Hz) than the Uniform pattern (90-360 Hz), the two patterns had the same entropy.

FIG. 10A provides the stimulation delivery and data collection timeline. Each black box rectangle indicates a period of four minutes during which either stimulation is turned off (DBS OFF) or turned on (DBS ON). During each 4-minute window, data collection, as further described below, occurred during two time periods of twenty seconds each. First, at about two minutes into the 4-minute window, data collection period "a" started, and second, at about three minutes and thirty seconds into the 4-minute window, data collection period "b" started.

FIG. 10B provides an overview of which data was analyzed. First, baseline data was obtained. This data was taken from data collection time period "b" in the "Pre-Baseline" 4-minute window. Next, for each patient, the trial "b" data collected during DBS ON times was analyzed and compared to the baseline data. If a certain period of trial "b" data collection was not completed, then trial "a" data was analyzed for that window for that patient.

Figure 11:
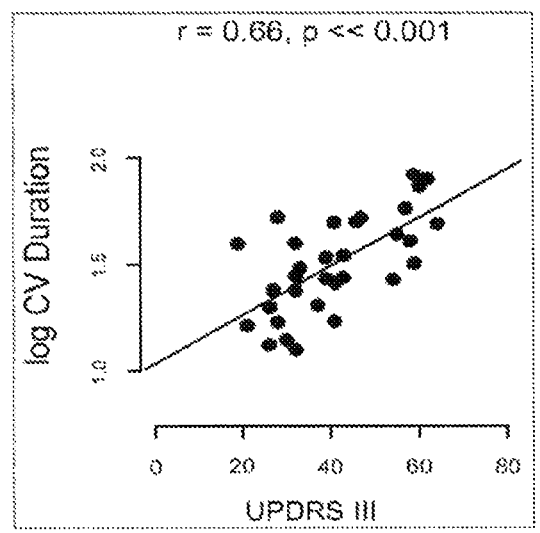
FIG. 11 depicts prior stimulation experimentation establishing key depression duration as being statistically significantly correlated to motor symptom severity.
Figure 12:
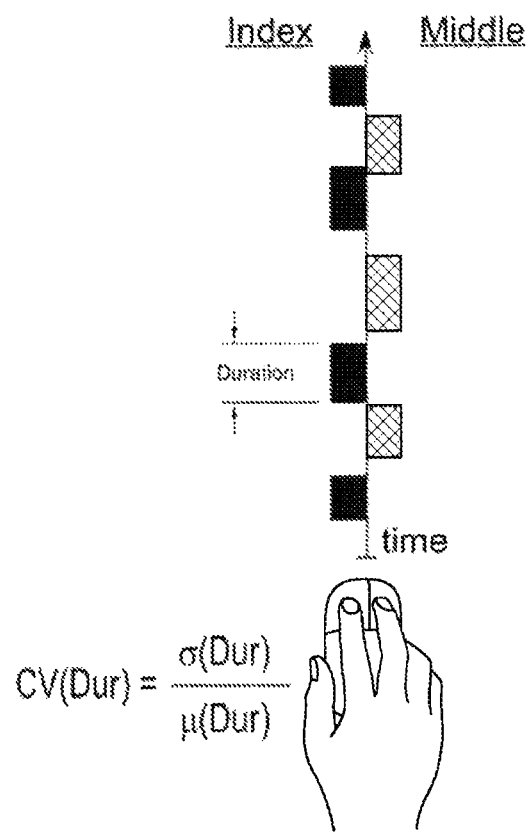
FIG. 12 depicts an exemplary embodiment of a portion of a stimulation response data collection system and associated method.
Figure 13A:
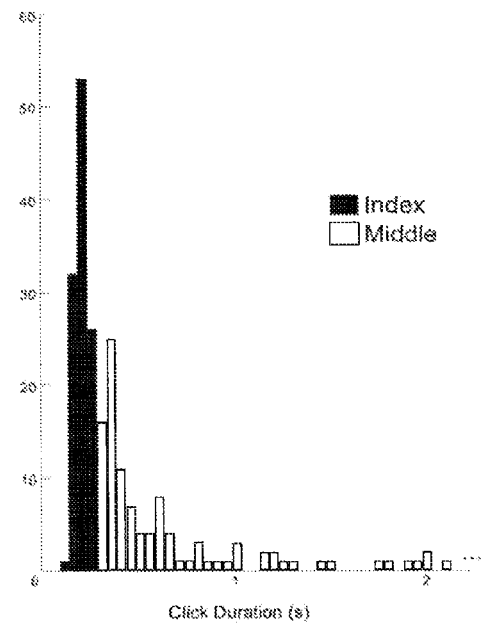
FIG. 13A depicts a histogram of click or button depression durations of a patient.
Figure 13B:
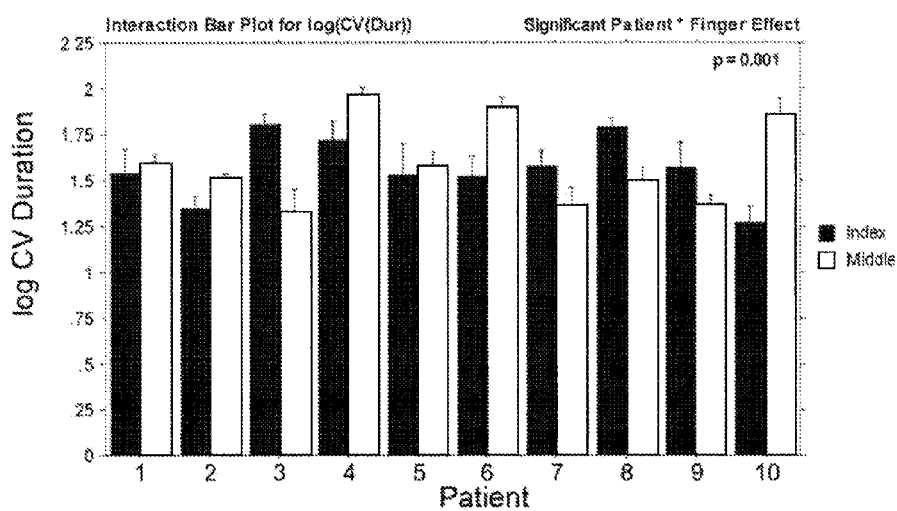
FIG. 13B is a bar plot indicating a statistically significant per patient finger effect.

With reference to FIGS. 11-14, the data collection methodology may now be explained. In FIG. 11, previously conducted experiments using a keyboard and with reference to both hands, it was found that the coefficient of variation of the time duration of the depression of a key on a keyboard was statistically significantly correlated to motor symptom severity. See Taylor Tavares, et al. (2005). To measure the effect of the DBS stimulation patterns according to the present invention, a two-button computer mouse was utilized, and the patient was instructed to, during the data collection times, alternate clicking a respective mouse button with their index finger and their middle finger. The time duration of the respective button clicks was then recorded by a computer and analyzed. Due to an observed greater variation in middle finger click duration across patients, as shown in FIGS. 13A and B, data from index finger clicks was thought more reliable and therefore analyzed. That is, since the collected click time durations for the index fingers and middle fingers were substantially differently distributed, the respective finger durations were not likely good candidates to be pooled for statistical analyses.

Figure 14:
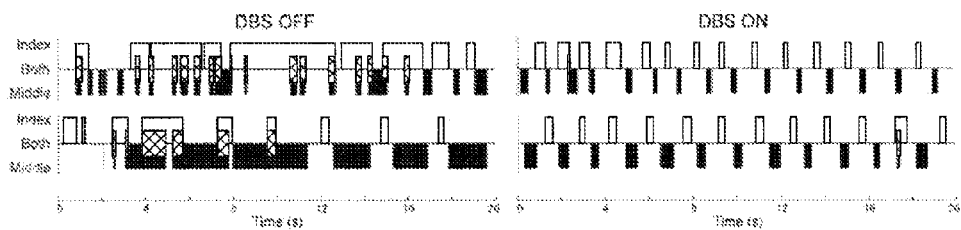
FIG. 14 is a timeline of button depression or click durations for two patients, one along the top line and one along the bottom line, while DBS is off (left) and while DBS is on (right), respectively.

FIG. 14 depicts click duration data collected from a first patient (on top) and a second patient (on bottom). As can be seen, during DBS OFF times, there was great variation in the click durations for each finger. Indeed, there is even substantial overlap with both fingers clicking the mouse buttons at the same time. As can be seen on the right for each patient, when stimulation patterns according to the present invention were applied, improvements can be seen both in click duration consistency, as well as reduced simultaneous clicking.

As demonstrated in FIG. 15, stimulation patterns and methods according to the present invention have been shown to increase the efficacy of such stimulation, preferably without substantially increasing the mean frequency of the stimulation over a generally accepted frequency range, and maintaining a constant geometric mean frequency. Smaller values on the bar graph's y-axis indicate better performance on a motor task executed during the application of the DBS patterns. Bars not labeled with the same letter are significantly different from one another.

As indicated earlier, the results were unexpected. In prior experimentation, greater variability in DBS stimulation correlated to a greater motor symptom severity. Not only were the results unexpected, but the results also cannot be explained with reference to generally accepted computer models that reflect expected behavior.

Figure 16A:
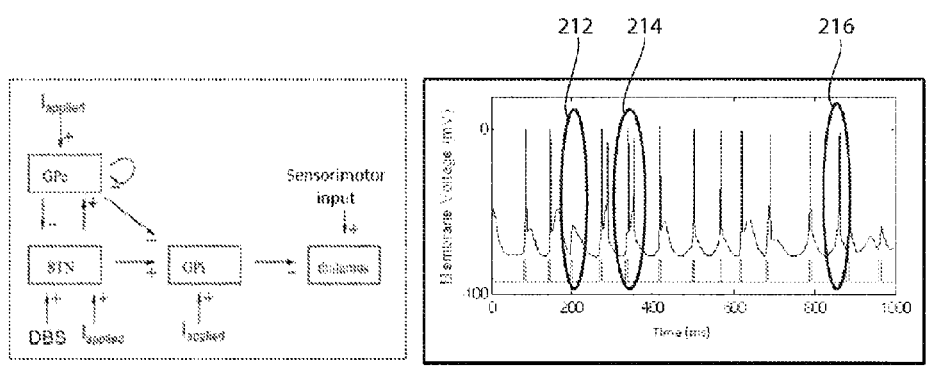
FIG. 16A depicts a generally accepted model used to generate thalamic neural responses to DBS and sensorimotor input (left) and types of errors that may be generated by such model (right).

FIG. 16A depicts, on the left, a generally accepted computer model from which thalamic neurological errors may be modeled. On the right, FIG. 16A shows examples of such errors. First, a "miss" error 212 is shown. That is, when a sensorimotor input is provided to the thalamus, a corresponding thalamic neuron response is expected, but does not show. Next, a "burst" error 214 is shown. A burst error occurs when more than one thalamic neuron response is generated in a short time window after a sensorimotor input. Finally, a "spurious" error 216 is a thalamic neuron response that is generated without the thalamus receiving a sensorimotor input.

In the experimental study the computer model is a biophysical model of the basal ganglia in a PD state including the STN, GPi, and external globus pallidus (GPe). Each nucleus of the basal ganglia model contains 10 single compartment neurons. Each GPe neuron sends inhibitory projections to two STN neurons, two GPI neurons, and two other GPe neurons. STN neurons may send excitatory projections to two GPe neurons and two GPi neurons. The biophysical properties of each neuron type were validated against experimental data and are described in detail elsewhere. Constant currents were applied to neurons in each nucleus to represent inputs from afferent projections that were not included in the model and produced firing rates that were consistent with observations in non-human primate models of PD and human patients with PD. For example, STN and GPi neurons received applied current of 33 $\mu A/cm^2$ and 21 $\mu A/cm^2$, respectively. Variability was added to the model by delivering a constant current to each GPe neuron randomly drawn from a normal distribution centered around 8 $\mu A/cm^2$ with a standard deviation of 2 $\mu A/cm^2$. STN DBS was applied by delivering the desired pattern of current pulses (amplitude 300 $\mu A/cm^2$; pulse width 0.3 ms) to each STN neuron.

Figure 16B:
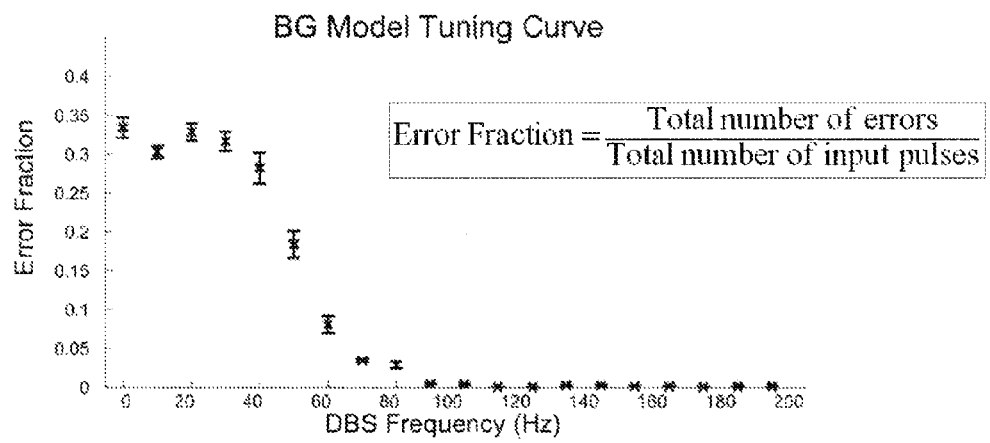
FIG. 16B depicts the DBS frequency-dependence of the model outcome measure, the error fraction, which mirrors the DBS frequency-dependence of motor symptoms.

As shown in FIG. 16B, DBS delivered to the model may reduce the error fraction, as defined, along a stimulation frequency range between about 100 Hz to about 200 Hz. This tuning curve of error fraction as a function of DBS frequency in the biophysical model parallels strongly the tuning curve of symptoms as a function of DBS frequency in patients with PD.

Figure 17A:
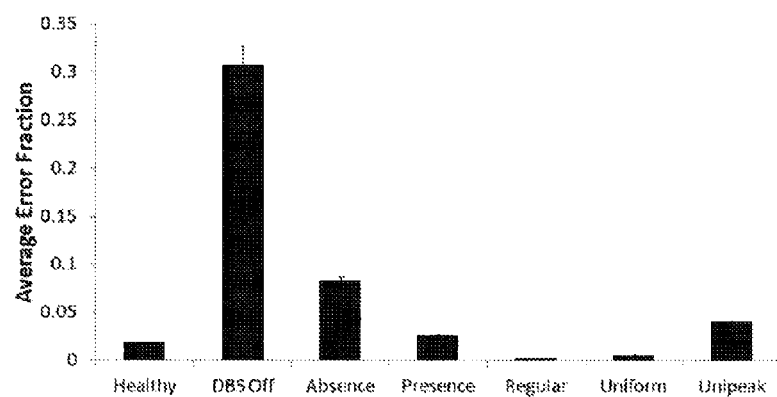
FIG. 17A is a graph of an average error fraction generated by the model of FIG. 16A when presented with the different temporal patterns of stimulation according to the present invention listed along the x-axis.
Figure 17B:
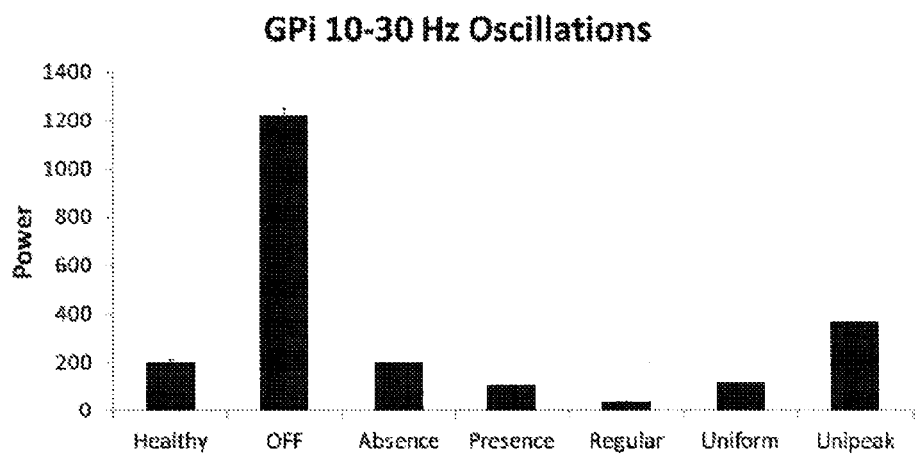
FIG. 17B is a graph of power of beta band oscillations in the GPI neurons of the model of FIG. 16A when presented with the different temporal patterns of stimulation according to the present invention listed along the x-axis.
Figure 17C:
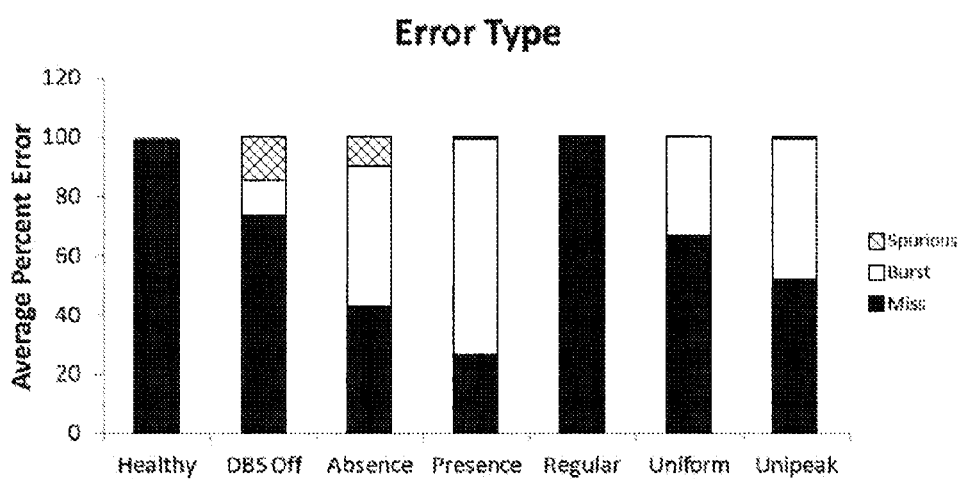
FIG. 17C is a graph of the percentage of errors generated grouped by type of error by the model of FIG. 16A when presented with the different temporal patterns of stimulation according to the present invention listed along the x-axis.

The observed improvements (FIG. 15) by the application of stimulation according to the present invention cannot be explained by the conventional wisdom embodied in the generally accepted computer model of thalamic response. By delivering the stimulation trains to the model, expected values are generated, as can be seen in FIGS. 17A-C. FIG. 17A shows average error fraction data generated by a generally accepted computer model. A lower average error fraction would seem to indicate an expected lower motor symptom severity as measured by click duration. As can be seen, the Regular stimulation pattern would be expected to generate a lower motor symptom severity than the patterns according to the present invention. However, as explained above and with reference to FIG. 15, the stimulation patterns according to the present invention performed better.

Also, stimulation patterns according to the present invention were expected to perform worse than previous Regular DBS trains based on an analysis of expected beta band oscillations generated by the model, as seen in FIG. 17B. There is some conventionally accepted correlation between beta band oscillations and slower motor response. That is, an increased strength or power of beta band oscillations is generally correlated to a higher motor symptom severity, or slower motor response. Examining expected beta band oscillations from the model, the prior Regular stimulation patterns would be expected to perform better than the stimulation patterns according to the present invention. However, as explained above and with reference to FIG. 15, the stimulation patterns according to the present invention performed better.

Furthermore, the success of the stimulation pattern trains according to the present invention does not appear to be explainable or correlated to the types of errors expected, or as generated by the model, as seen in FIG. 17C.

Thus, conventional experiments and associated wisdom as embodied in generally accepted models all predicted that stimulation pattern trains according to the present invention would fail, or at least perform worse than conventional Regular DBS stimulation patterns. In the end, however, it was found that stimulation pattern trains according to the present invention performed better than prior trains.

Further, post-hoc testing also revealed significant differences between stimulation patterns. During Absence, Presence, and Uniform DBS, the tap duration variability, a validated measure of symptom severity, was lower than during Regular DBS, indicating that these patterns improved bradykinesia in PD more effectively than the temporally regular stimulation pattern used clinically. Motor task performance (Log CV Duration) during the Unipeak and Regular patterns was similar, see FIG. 15. Consequently, tap duration variability during the Absence, Presence, and Uniform stimulation patterns was tower than during the Unipeak pattern. When individually added to the repeated measures ANOVA statistical model, there was not a significant effect of surgical target, medication state, sedation status, or switching to a bipolar electrode configuration.

The responses to the different temporal patterns of stimulation were consistent across subjects. In 9/10 subjects, motor performance was better during the Absence and Uniform patterns compared to the Regular pattern. Motor performance was superior during Presence DBS compared to Regular stimulation in 7/10 subjects. Motor performance was improved during stimulation compared to Baseline in 80-100% of the subjects depending on the pattern.

Figure 18A:
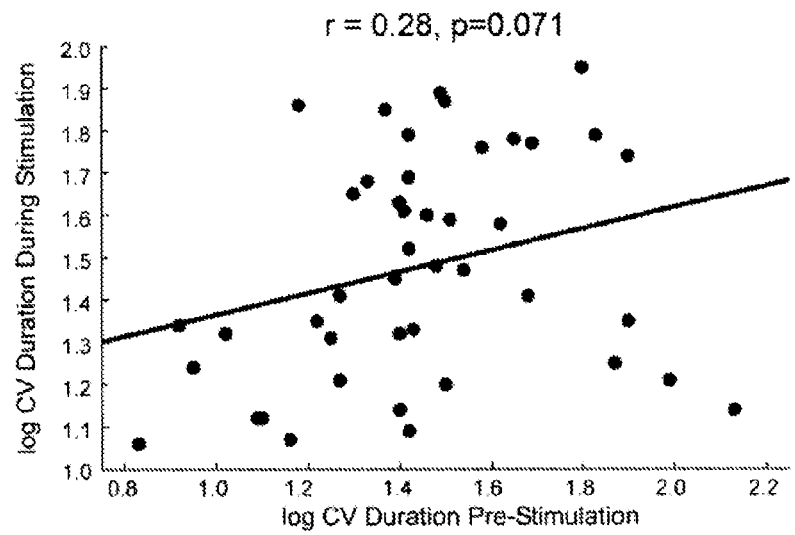
FIG. 18A is a graph of the log CV Duration during stimulation when presented with log CV Duration pre-stimulation listed along the x-axis.

Motor performance during the stimulation patterns was weakly correlated with motor performance during the preceding stimulation off period, see FIG. 18A. This suggested that changes in finger tap duration variability between stimulation patterns were caused by the stimulation patterns themselves, and were not a reflection of fluctuations in baseline motor performance.

Figure 18B:
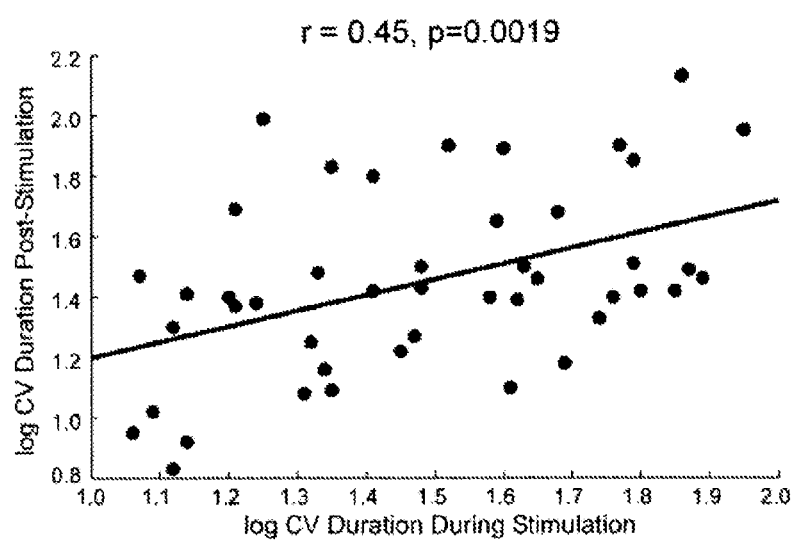
FIG. 18B is a graph of the log CV Duration post-stimulation when presented with log CV Duration during stimulation listed along the x-axis.

Instead, and consistent with the time course of the action of DBS in PD, motor performance during the stimulation off period following each stimulation pattern reflected the motor performance during the preceding pattern of stimulation, as demonstrated by significant correlations between finger tap duration variability during the stimulation pattern and during the subsequent stimulation off periods, see FIG. 18B.

Figure 19A:
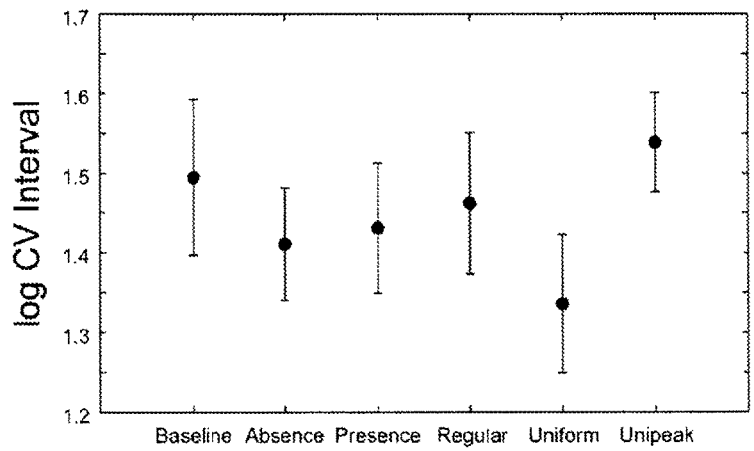
FIG. 19A is a graph of the log CV Interval when presented with the different temporal patterns of stimulation according to the present invention listed along the x-axis.
Figure 19B:
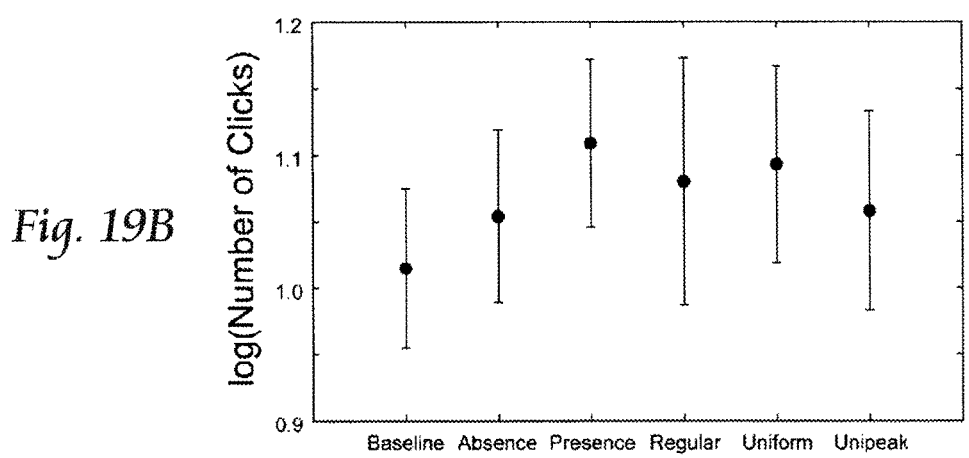
FIG. 19B is a graph of the log number of clicks when presented with the different temporal patterns of stimulation according to the present invention listed along the x-axis.

The log-transformed coefficient of variation of the intervals between finger taps (log CV Interval) exhibited the same pattern of motor performance across stimulation patterns as log CV Duration, See FIG. 19A. The finger tap timing was the most irregular, on average, during Baseline and the Unipeak pattern of stimulation, and the average log CV Interval during Absence, Presence, and Uniform DBS was lower than it was during Regular DBS. The log-transformed rate of finger tapping exhibited a similar dependence on stimulation pattern. The fewest button presses occurred during Baseline (stimulation off), and the most occurred during the Presence pattern of stimulation, see FIG. 19B.

It was discovered that some temporal patterns of DBS improved motor performance more than regular stimulation, but there was also a desire to determine which features of the stimulation patterns influenced the efficacy of DBS. Therefore, the effects of bursts, pauses, and irregularity in the stimulation patterns were evaluated by pooling motor performance data across stimulation trains that shared the feature of interest. Data during Presence and Unipeak DBS were pooled into a "Bursts" group and the remaining patterns into a "No Bursts" group; measurements made during Absence and Unipeak DBS were pooled into the "Pauses" group; and measurements from Uniform and Unipeak DBS were pooled into the "Irregular" group.

Quantitative measurement of the effects of different temporal patterns of DBS on bradykinesia in subjects with PD and oscillatory activity of model neurons revealed three central findings. First, the pattern of stimulation, and not simply the stimulation rate, was an important factor in the clinical efficacy of DBS, as demonstrated by the different levels of performance on a simple motor task during different temporal patterns of stimulation all of which had the same mean frequency. Second, some non-regular patterns of stimulation relieved motor symptoms in PD more effectively than the temporally regular stimulation pattern used clinically. Third, the differential efficacy of DBS patterns was strongly correlated with the pattern's ability to suppress beta band oscillatory activity in a computational model of the basal ganglia.

Figure 20:
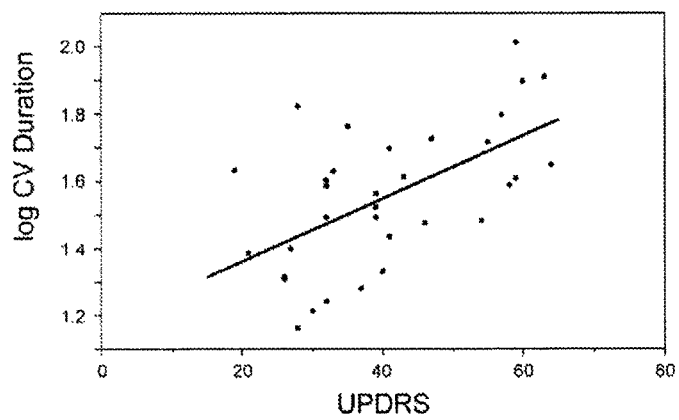
FIG. 20 is a graph depicting prior stimulation experimentation establishing log CV Duration as being statistically significantly correlated to UPDRS, or motor symptom severity.

The correlations between log CV Durations and the bradykinesia and rigidity UPDRS motor subscores are significant, but it remains unclear whether these non-regular patterns of stimulation would ameliorate other parkinsonian motor signs. UPDRS motor score improvements across stimulation patterns were predicted from log CV Duration values using the correlation between these two variables, see FIG. 20. Changes in log CV Duration from Baseline for each patient were multiplied by the correlation coefficient (R=0.58) and scaled by the gain (80 UPDRS motor points per 0.75 log unit) to predict stimulation-induced shifts in UPDRS motor scores across stimulation patterns. The difference ill log CV Duration scores between Regular stimulation and Absence, Presence, and Uniform patterns represented an improvement of 12-15 UPDRS motor score points on average, suggesting that these temporal patterns of stimulation provide clinically meaningful improvement over temporally regular stimulation.

Figure 21A:
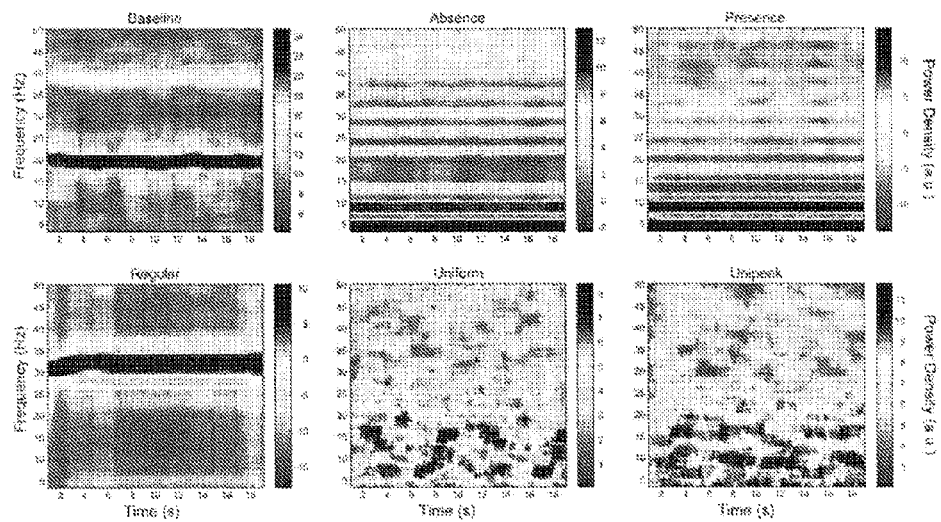
FIG. 21A is a series of charts showing power density for the different temporal patterns of stimulation according to the present invention.
Figure 21B:
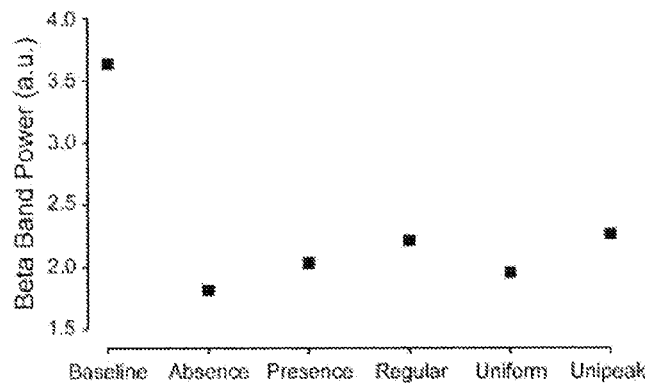
FIG. 21B is a graph showing beta band power for the different temporal patterns of stimulation according to the present invention.
Figure 21C:
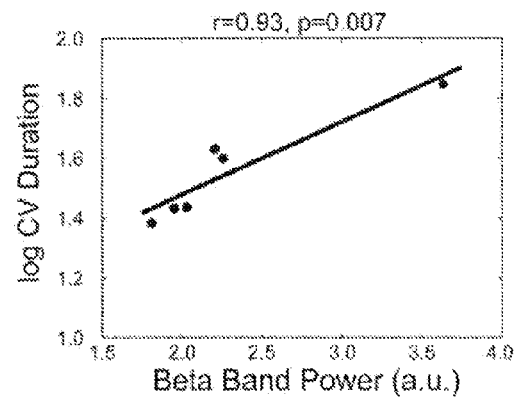
FIG. 21C is a graph depicting the log CV duration being correlated to beta power.

The present invention shows that different temporal patterns of DBS differentially suppressed oscillatory activity in a computational model of the basal ganglia. FIG. 21A shows spectrograms of GPi spike times from the computational model of the basal ganglia in the PD state across stimulation conditions. FIG. 21B shows that changes in beta band oscillatory power during delivery in the biophysical model of different temporal patterns of DBS were strongly correlated with changes in symptoms when the same patterns of stimulation were delivered to human patients with PD. FIG. 21C shows the correlation between the log CV Duration and beta power in arbitrary units.

Oscillatory and synchronized neural activity specific frequency bands appear to be related to motor performance in patients with PD, and the non-regular patterns of stimulation that were most effective may be most able to override or otherwise disrupt pathological oscillations or synchronization in the basal ganglia. Indeed, the degree of suppression of the oscillatory activity in the model neurons matched the clinical efficacy of the patterns during the finger tapping task remarkably well, suggesting that the efficacy of these patterns of DBS depended on their ability to suppress, disrupt, or otherwise regularize pathological activity in the basal ganglia.

In using previous systems and/or methods, the frequency or the amplitude of the DBS is increased when a patient or clinician desires a more pronounced effect from the stimulation. Unfortunately, this inevitably leads to a shorter battery life for the implantable pulse generator system because of the higher demands placed on it. This calls for more frequent battery recharging or surgery to replace non-rechargeable implantable pulse generator. Instead of only increasing the intensity (amplitude or frequency) of stimulation and reaping the consequences of those actions, it is beneficial to increase the efficacy of the stimulation by simply changing the pattern of stimulation. That is exactly what the technology described in this invention does. It provides a greater level of symptom suppression for the patient while using an average frequency of stimulation similar to frequencies previously used in standard practice.

It is contemplated that non-regular stimulation patterns or trains can be readily applied to deep brain stimulation, to treat a variety of neurological disorders, such as Parkinson's disease, movement disorders, epilepsy, and psychiatric disorders such as obsessive-compulsion disorder and depression. The non-regular stimulation patterns or trains can also be readily applied to other classes electrical stimulation of the nervous system including, but not limited to, cortical stimulation, spinal cord stimulation, and peripheral nerve stimulation (including sensory and motor), to provide the attendant benefits described above and to treat diseases such as but not limited to Parkinson's Disease, Essential Tremor, Movement Disorders, Dystonia, Epilepsy, Pain, psychiatric disorders such as Obsessive Compulsive Disorder, Depression, and Tourette's Syndrome.

It is contemplated that the systems and methodologies make it possible to determine the effects of the temporal pattern of DBS on simulated and measured neuronal activity, as well as motor symptoms in both animals and humans. The methodologies make possible the qualitative determination of the temporal features of stimulation trains.

According to the systems and methods according to the present invention, it has further been demonstrated that stimulation having a pattern, preferably a repeating pattern, of non-regular stimulation at a high average frequency may increase the efficacy of electrical stimulation provided to relieve symptoms of neurological disorders, such as those treated with DBS. A system or method according to the present invention may generate or utilize a higher frequency (about 100 to about 200 Hertz) non-regular pattern of DBS for the treatment or alleviation of symptoms of neurological disorders.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

INCORPORATED APPENDICES

McIntyre C C, Grill W M, Sherman D L, Thakor N V (2004) Cellular effects of deep brain stimulation: model-based analysis of activation and inhibition. J Neurophysiol 91:1457-1469, incorporated as Appendix A, hereto.

Birdno M J "Analyzing the mechanisms of thalamic deep brain stimulation: computational and clinical studies". Ph.D. Dissertation. Department of Biomedical Engineering, Duke University, Durham, N.C., USA, August 2009, incorporated as Appendix B, hereto.

Rubin J E, Terman D (2004) High frequency stimulation of the subthalamic nucleus eliminates pathological thalamic rhythmicity in a computational model. J Comput Neurosci 16:211-235, incorporated as Appendix C, hereto.

Brocker D T, Swan B D, Turner D A, Gross R E, Tatter S B, Koop M M, Bronte-Stewart H, Grill W M "Improved Efficacy of Temporally Non-Regular Deep Brain Stimulation in Parkinson's Disease" Department of Biomedical Engineering, Duke University, Durham, N.C., USA, incorporated as Appendix D, hereto.

OTHER REFERENCES

Dorval, A. D., A. M. Kuncel, et al. (2010). "Deep Brain Stimulation Alleviates Parkinsonian Bradykinesia by Regularizing Palladial Activity." J Neurophysiol 104(2): 911-921.

Feng X J, Shea-Brown E, Greenwald B, Kosut R. Rabitz H (2007) Optimal deep brain stimulation of the subthalamic nucleus—a computational study. J Comput Neurosci. 23(3):265-282.

Grefenstette J J (1986) Optimization of Control Parameters for Genetic Algorithms. IEEE Transactions on Systems, Man and Cybernetics 16:122-128.

Taylor Tavares, A. L., G. S. X. E. Jefferis, et al. (2005). "Quantitative measurements of alternating finger tapping in Parkinson's disease correlate with UPDRS motor disability and reveal the improvement in fine motor control from medication and deep brain stimulation." *Movement Disorders* 20(10): 1286-1298.

Having thus described the invention, we claim:

1. A medical stimulation system comprising:
an implantable pulse generator coupled to an electrode configured to be implanted and having a microprocessor including a computational model of basal ganglia to output a repeating succession of non-regular stimulation pulse trains comprising at least two plurality of stimulation pulses with non-random and differing intervals free of stimulation pulses between each of the plurality of pulses; and
the implantable pulse generator transmitting, through the electrode to neurological tissue in a brain, spinal cord, or near a peripheral nerve of a patient, the stimulation pulse trains.

2. The medical stimulation system of claim 1, wherein a first frequency of a first of the at least two plurality of stimulation pulses is different from a second frequency of a second one of the at least two plurality of stimulation pulses.

3. The medical stimulation system of claim 1, wherein the electrode is implanted in a brain of a patient.

4. The medical stimulation system of claim 1, wherein the repeating succession of non-regular stimulation pulse trains reduces symptoms of Parkinson Disease.

5. The medical stimulation system of claim 4, wherein at least one symptom reduced includes a motor symptom.

6. The medical stimulation system of claim 1, wherein the the output of simulation pulse trains are structured to suppress beta band oscillatory activity.

7. The medical stimulation system of claim 1, wherein the the output of stimulation pulse trains suppresses oscillatory neural activity.

* * * * *